(12) United States Patent
Moinet et al.

(10) Patent No.: US 7,491,733 B2
(45) Date of Patent: Feb. 17, 2009

(54) BICYCLIC GUANIDINE DERIVATIVES AND THERAPEUTIC USES THEREOF

(75) Inventors: Gerard Moinet, Orsay (FR); Daniel Cravo, Sartrouville (FR)

(73) Assignee: Merck Patent GmbH, Darmstadt (DE)

( * ) Notice: Subject to any disclaimer, the term of this patent is extended or adjusted under 35 U.S.C. 154(b) by 347 days.

(21) Appl. No.: 10/472,228

(22) PCT Filed: Feb. 27, 2002

(86) PCT No.: PCT/EP02/02094

§ 371 (c)(1),
(2), (4) Date: Sep. 22, 2003

(87) PCT Pub. No.: WO02/076963

PCT Pub. Date: Oct. 3, 2002

(65) Prior Publication Data

US 2004/0122040 A1   Jun. 24, 2004

(30) Foreign Application Priority Data

Mar. 21, 2001 (FR) .................................. 01 03843

(51) Int. Cl.
| | |
|---|---|
| A61K 31/44 | (2006.01) |
| A61K 31/425 | (2006.01) |
| A61K 31/42 | (2006.01) |
| A61K 31/415 | (2006.01) |
| C07D 215/12 | (2006.01) |
| C07D 413/00 | (2006.01) |
| C07D 235/00 | (2006.01) |
| C07D 333/00 | (2006.01) |
| A01K 43/42 | (2006.01) |

(52) U.S. Cl. ................ 514/301; 514/302; 514/303; 514/367; 514/375; 514/394; 546/114; 546/115; 546/176; 548/152; 548/215; 548/309.7; 548/469; 549/49; 549/462

(58) Field of Classification Search ................ None
See application file for complete search history.

(56) References Cited

U.S. PATENT DOCUMENTS

| | | | |
|---|---|---|---|
| 3,426,043 A | 2/1969 | Green et al. | |
| 3,428,653 A | 2/1969 | Bell | |
| 3,700,697 A * | 10/1972 | Bailey ................. | 549/467 |
| 3,855,242 A | 12/1974 | Chapman et al. | |
| 4,260,628 A | 4/1981 | Jonas et al. | |

FOREIGN PATENT DOCUMENTS

| | | |
|---|---|---|
| FR | 1502346 A | 2/1968 |
| HU | P9102206 | 1/2000 |

OTHER PUBLICATIONS

Chapman et al. Pharmacologically active benzo[b]thiophen derivatives. Analogues of tryptamine and heteroauxin Journal of the Chemical Society Section C: Organic Chemistry 1969, 12, 1612-1616.*
N.B. Chapman et al : "Pharmacologically active benso'b!thionphen deriivatives. Analogues of tryptamine and heteroauxin" Journal of the Chemical Society, Section C: Organic Chemistry, No. 12, 1969, pp. 1612-1616.
K. S. Sharma et al.; "Condensed Heterocyclics: Part XVI-Synthesis of N-Substituted 4-Bromo-2-guandinomethylbenzo[b]thiophenes"; Indian Journal of Chemistry: vol. 23B, Jan. 1984; pp. 38-41.

* cited by examiner

Primary Examiner—Johann R. Richter
Assistant Examiner—Ernst V Arnold
(74) Attorney, Agent, or Firm—Millen, White, Zelano & Branigan, P.C.

(57) ABSTRACT

The invention relates to compounds of general formula (I), in which A, X, Y and R1 are defined in Claim 1. These compounds may be used in the treatment of pathologies associated with insulin resistane syndrome.

17 Claims, No Drawings

BICYCLIC GUANIDINE DERIVATIVES AND THERAPEUTIC USES THEREOF

The present invention relates to bicyclic guanidine derivatives that are useful in the treatment of pathologies associated with insulin resistance syndrome.

Bicyclic guanidine derivatives with antihypertensive or antimicrobial properties have been described in U.S. Pat. Nos. 3,855,242, 4,260,628 and Yaoxue Xuebao, 1982, 17(3), 229-232.

The present invention is directed towards providing novel bicyclic guanidine compounds with novel properties.

The present invention therefore relates to a compound of the general formula (I)

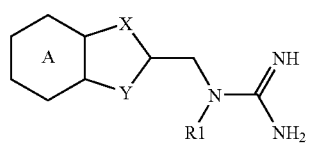

in which
A represents a benzene or pyridine ring which is optionally substituted by one or more of the following groups:
  branched or unbranched ($C_1$-$C_{20}$)alkyl,
  OR2, where R2 represents:
    H,
    branched or unbranched ($C_1$-$C_5$)alkyl,
    ($C_3$-$C_8$)cycloalkyl, or
    benzyl,
  NR3R4, where R3 and R4 represent, independently of each other:
    H,
    branched or unbranched ($C_1$-$C_{20}$)alkyl,
    benzyl,
    acetyl,
    ($C_3$-$C_8$)cycloalkyl,
    or alternatively R3 and R4 together form a 3- to 8-membered ring including a nitrogen atom,
  SR5, where R5 represents:
    H,
    branched or unbranched ($C_1$-$C_5$)alkyl,
    ($C_3$-$C_8$)cycloalkyl, or
    benzyl,
  halogen
  cyano
  nitro
  $CO_2$R6, where R6 represents:
    H or
    branched or unbranched ($C_1$-$C_5$)alkyl, or
  trifluoromethyl,
X represents a —CH═, —$CH_2$—, —N═ or —NH— radical,
Y represents a $CH_2$ radical, an oxygen or sulfur atom or a group —NR7, where R7 represents:
  H,
  branched or unbranched ($C_1$-$C_5$)alkyl,
  benzyl,
  ($C_3$-$C_8$)cycloalkyl, or
  a $CH_2CO_2H$ group,
R1 represents one of the following groups
  H,
  branched or unbranched ($C_1$-$C_5$)alkyl, or
  benzyl with the exception of the compounds of the formula (I) in which:
a—A represents a benzene ring, X represents —CH═ or —$CH_2$—, Y represents an oxygen atom and R1 is a hydrogen atom;
b—A represents a benzene ring substituted in position 5' of the double ring with a halogen atom, X represents —CH═, Y represents a sulfur atom and R1 is a hydrogen atom,
c—A represents an unsubstituted benzene ring, X represents —$CH_2$—, R1 is a hydrogen atom or a branched or unbranched ($C_1$-$C_5$)alkyl radical and Y represents NR7, where R7 represents a hydrogen atom, a branched or unbranched ($C_1$-$C_5$)alkyl radical or a benzyl radical,
d—A represents an unsubstituted benzene ring, X represents —CH═, R1 is a hydrogen atom and Y represents NR7, where R7 represents an ethyl radical, and also the tautomeric, enantiomeric, diastereoisomeric and epimeric forms, the solvates and the pharmaceutically acceptable salts.

Among the branched or unbranched $C_1$-$C_{20}$ alkyl radicals that may especially be mentioned are the methyl, ethyl, propyl, isopropyl, butyl, sec-butyl, tert-butyl, pentyl, hexyl, heptyl, octyl, nonyl, decyl, dodecyl, pentadecyl and hexadecyl radicals.

One particular group of compounds of the formula (I) is that in which the alkyl radicals are $C_1$-$C_5$ alkyl radicals.

Among the $C_3$-$C_8$ cycloalkyl radicals that may especially be mentioned are cyclopropyl, cyclopentyl, cyclohexyl and cycloheptyl radicals.

3- to 8-membered rings including a nitrogen atom that may especially be mentioned are aziridine, pyrrolyl, imidazolyl, pyrazolyl, indolyl, indolinyl, pyrrolidinyl, piperazinyl and piperidyl rings.

Another particular group of compounds of the formula (I) is that in which A represents an optionally substituted benzene ring. One particular sub-group is the one in which X represents a —CH═ radical or a —$CH_2$— radical. Another particular sub-group is the one in which X represents an —N═ radical or an —NH— radical.

Another particular group of compounds of the formula (I) is the one in which Y represents a —$CH_2$— radical, a sulfur atom or a group —NR7, where X preferably represents —CH═ or —$CH_2$.

One sub-group targets these compounds of the formula (I) in which A represents a substituted benzene ring, more preferably a benzene ring mono-substituted in a position other than position 5' of the double ring, or a benzene ring substituted by at least two groups.

One particular sub-group of compounds of the formula (I) is the one in which Y is a sulfur atom and A represents a benzene ring monosubstituted in a position other than position 5' of the double ring, or a benzene ring substituted by at least two groups.

Another particular sub-group of compounds of the formula (I) is the one in which Y is a group —NR7 and A represents a substituted benzene ring.

Another particular group of compounds of the formula (I) is the one in which Y represents a —$CH_2$— radical, a sulfur atom or a group —NR7, where A preferably represents a substituted benzene ring, more preferably a benzene ring monosubstituted in a position other than position 5' of the double ring, or a benzene ring substituted by at least two groups.

The invention also relates to the tautomeric, enantiomeric, diastereo-isomeric and epimeric forms of the compounds of the general formula (I).

The compounds of the general formula (I) contain basic nitrogen atoms that may be monosalified or disalified with organic or mineral acids.

The compounds of the general formula (I) may be prepared from a compound of the general formula (II):

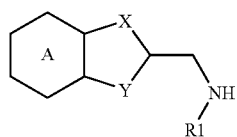

in which A, X, Y and R1 have the definitions specified above, and according to the methods for obtaining a guanidine that are described in the literature.

By way of example, these methods are especially described in the following literature: Tetrahedron Letters, 1993, 34(48), 7677-7680; Tetrahedron Letters, 1993, 34(21), 3389-3392; Tetrahedron Letters, 1996, 37(14), 2483-2486; WO 98/52917; Journal of Medicinal Chemistry, 1990, 33(1), 434-444; Journal of Organic Chemistry, 1998, 63, 3804-3805; WO 94/29269; Tetrahedron Letters, 1994, 35(7), 977-980; Journal of Organic Chemistry, 1992, 57, 2497-2502; Synthesis, 1986, 777-779; Synthetic Communications, 1987, 17(15), 1861-1864.

The compounds of the formula (II) are prepared by simple and standard reactions readily available to those skilled in the art. By way of example, the following references illustrate these syntheses: Oppi Briefs, 1996, 28(6), 702-704; Heterocycles, 1988, 27(6), 1421-1429; Pharmazie, 1999, 54(9), 651-654; WO 95/09159; WO 91/09023; WO 97/42183; Synthetic Communications, 1993, 23(6), 743-748; Journal of the American Chemical Society, 1952, 74, 664-665; DE 2 739 723; Journal of Medicinal Chemistry, 1994, 37(23), 3956-3968; WO 93/17025; WO 96/00730; Heterocycles, 1995, 41(3), 477-486; Journal of Medicinal Chemistry, 1968, 11, 1164-1167; Monatshefte für Chemie, 1957, 1087-1094; Journal of Medicinal Chemistry, 1989, 32, 1988-1996.

The compounds according to the present invention, and more generally the compounds of the formula (I)

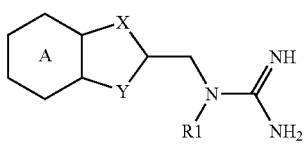

in which:
A represents a benzene or pyridine ring optionally substituted by one or more of the following groups:
  branched or unbranched ($C_1$-$C_{20}$)alkyl,
  OR2, where R2 represents:
    H,
    branched or unbranched ($C_1$-$C_5$)alkyl,
    ($C_3$-$C_8$)cycloalkyl, or
    benzyl,
  NR3R4, where R3 and R4 represent, independently of each other:
    H,
    branched or unbranched ($C_1$-$C_{20}$)alkyl,
    benzyl,
    acetyl,
    ($C_3$-$C_8$)cycloalkyl,
    or alternatively R3 and R4 together form a 3- to 8-membered ring including a nitrogen atom,
  SR5, where R5 represents:
    H,
    branched or unbranched ($C_1$-$C_5$)alkyl,
    ($C_3$-$C_8$)cycloalkyl, or
    benzyl,
  halogen
  cyano
  nitro
  $CO_2$R6, where R6 represents:
    H or
    branched or unbranched ($C_1$-$C_5$)alkyl, or
  trifluoromethyl,
X represents a —CH═, —$CH_2$—, —N═ or —NH— radical,
Y represents a $CH_2$ radical, an oxygen or sulfur atom or a group —NR7, where R7 represents:
  H,
  branched or unbranched ($C_1$-$C_5$)alkyl,
  benzyl,
  ($C_3$-$C_8$)cycloalkyl, or
  a $CH_2CO_2H$ group,
R1 represents one of the following groups
  H,
  branched or unbranched ($C_1$-$C_5$)alkyl, or
  benzyl, and also the tautomeric, enantiomeric, diastereoisomeric and epimeric forms thereof, the solvates and the pharmaceutically acceptable salts thereof, are useful in the treatment of pathologies associated with insulin resistance syndrome (syndrome X).

Insulin resistance is characterised by a reduction in the action of insulin (cf. Presse Médicale, 1997, 26(No. 14), 671-677) and is involved in a large number of pathological conditions, such as diabetes and more particularly non-insulin-dependent diabetes (type II diabetes or NIDDM), dyslipidaemia, obesity and also certain microvascular and macrovascular complications, for instance atherosclerosis, retinopathies and neuropathies.

In this respect, reference will be made, for example, to Diabetes, Vol. 37, 1988, 1595-1607; Journal of Diabetes and its Complications, 1998, 12, 110-119 or Horm. Res., 1992, 38, 28-32.

The compounds of the invention especially have strong hypoglycaemiant activity.

The present invention thus also relates to pharmaceutical compositions comprising, as active principle, a compound according to the invention.

The pharmaceutical compounds according to the invention may be presented in various forms intended for parenteral, oral, rectal, permucous or percutaneous administration.

They will therefore be presented in the form of injectable solutions or suspensions or multi-dose bottles, in the form of plain or coated tablets, sugar-coated tablets, wafer capsules, gel capsules, pills, cachets, powders, suppositories or rectal capsules, solutions or suspensions, for percutaneous use in a polar solvent, or for permucous use.

The excipients that are suitable for such administrations are cellulose derivatives, microcrystalline cellulose derivatives, alkaline-earth metal carbonates, magnesium phosphate, starches, modified starches and lactose for the solid forms.

For rectal use, cocoa butter or polyethylene glycol stearates are the preferred excipients.

For parenteral use, water, aqueous solutions, physiological saline and isotonic solutions are the vehicles that are the most suitable for use.

The dosage may vary within a wide range (0.5 mg or less, to 1000 mg) depending on the therapeutic indication and the route of administration, and also the age and weight of the individual.

The examples that follow illustrate the preparation of compounds of the formula (I).

EXAMPLE 1

Synthesis of 2-(aminoiminomethyl(methylamino) methyl)-benzothiazole hydrochloride Step 1: 2-chloromethylbenzothiazole (A)

Chloroacetyl chloride (81.6 ml) is added dropwise to a solution composed of 2-aminothiophenol (112 ml, 1.04 mol), dichloromethane (1.2 l) and three drops of dimethylformamide, while the temperature is kept below 40° C. After stirring for 18 hours, the precipitate formed is filtered off by suction and then dissolved in a minimum amount of water. This aqueous phase is extracted with pentane and the extracts are concentrated under vacuum at room temperature, giving 120 g (65%) of a flaky solid.

$^1$H NMR (DMSO-d$_6$, 200 MHz): δ: 8.32, d, 1H, aromatic H; 8.21, d, 1H, aromatic H; 7.77-7.63, m, 2H, aromatic H, 5.43, s, 2H, CH$_2$Cl Step 2: 2-methylaminomethylbenzothiazole (B)

A (115 g, 0.62 mol) and 580 ml of an aqueous 40% methylamine solution are heated at 60° C. in an autoclave for 18 hours. The reaction medium is concentrated and the residue is purified on a column of silica (7/3 petroleum ether/dichloromethane) to give 96 g (87%) of an orange-coloured oil.

$^1$H NMR (DMSO-d$_6$, 200 MHz): δ: 8.03-7.39, m, 4H, aromatic H; 4.24, s, 1H, CH$_2$; 2.61, s, 3H, CH$_3$ Step 3: 2-(aminoiminomethyl(methylamino)methyl)benzothiazole hydrochloride 55.7 g (0.449 mol) of aminoiminomethylsulfonic acid are added portionwise to a solution composed of dimethylformamide (400 ml) and B (80 g, 0.449 mol) cooled to 5° C., while the temperature is kept below 5° C. After stirring for 48 hours, the reaction medium is cooled to 5° C. and 75 ml (0.9 mol) of concentrated hydrochloric acid are added. After stirring for 1 hour, the solution is concentrated and the remaining oil is taken up in acetonitrile. The precipitate formed is filtered off by suction and then recrystallised from water to give 40 g (35%) of a white solid.

m.p.=203-205° C. $^1$H NMR (DMSO-d$_6$, 200 MHz): δ: 8.32, d, 1H, aromatic H; 8.25-7.40, m, 8H, aromatic H, NH and HCl; 5.20, s, 2H, CH$_2$; 3.10, s, 3H, NCH$_3$ $^{13}$C NMR (DMSO-d$_6$, 50 MHz): δ: 168.32, 159.08, 154.12, 136.33, quaternary C; 128.20, 127.27, 124.30 and 124.15, aromatic CH; 53.19, CH$_2$; 38.88, NCH$_3$

EXAMPLE 2

Synthesis of 2-(aminoiminomethylamino)methylbenzimidazole hydrochloride

Step 1: 2-aminomethylbenzimidazole (C)

A solution of 2-aminoaniline (27 g, 0.25 mol), glycine (27.7 g, 0.37 mol) and 250 ml of 5.5M hydrochloric acid is refluxed for 30 hours and then stored in a refrigerator for 24 hours. The precipitate formed is filtered off with suction and then taken up in 400 ml of methanol and treated with carbon black. The mixture is filtered and the solvent is removed to give 22 g (49%) of a white solid.

m.p.=81-83° C.

$^1$H NMR (DMSO-D$_6$, 200 MHz): δ: 7.40-6.90, m, 4H, aromatic H; 3.70, s, 2H, CH$_2$ Step 2: 2-(aminoiminomethylamino)methylbenzimidazole hydrochloride A solution of C (15 g, 0.101 mol), 1-(aminoiminomethyl)pyrazole hydrochloride (15 g, 0.102 mol) and 50 ml of dioxane is refluxed for 18 hours and then concentrated to dryness. The crude product is taken up in methanol (300 ml) and treated with carbon black. After filtration and concentration, the residue is taken up in a minimum amount of water and the remaining insoluble material is removed by filtration. The solution is then freeze-dried to give 14 g (62%) of a white solid.

m.p.=171-173° C.

$^1$H NMR (DMSO-d$_6$, 200 MHz): δ: 8.20-7.10, m, 8H, aromatic H, NH and HCl; 4.60, s, 2H, CH$_2$ $^{13}$C NMR (DMSO-d$_6$, 50 MHz): δ: 158.56, 151.26, 138.98, quaternary C; 122.88, 115.76, aromatic CH; 40.32, CH$_2$

EXAMPLE 3

Synthesis of 2-(aminoiminomethylamino)methylindane sulfate

Step 1: 2-methylcarboxyindane (D)

A solution of α,α'-dibromo-o-xylene (203.51 g, 0.77 mol) in 1.5 l of ether is added to a solution of diethyl malonate (127 g, 0.79 mol), sodium methoxide (314 ml, 1.70 mol), ethanol (100 ml) and ether (500 ml). The mixture is refluxed for 5 hours, then filtered, and finally concentrated. The residue is taken up in 500 ml of water. 173 g of potassium hydroxide are added, and the mixture is refluxed for 18 hours. The reaction medium is poured into a hydrochloric acid solution and the precipitate formed is filtered off by suction and then dried. The solid obtained is maintained at 200° C. for 20 minutes and the new solid obtained is recrystallised from 400 ml of heptane. The crystals obtained are taken up in 400 ml of methanol and, after 5 drops of concentrated sulfuric acid have been added, the mixture is refluxed for 4 hours and then concentrated. The residue is dissolved in 600 ml of ether. This ether phase is washed with saturated sodium bicarbonate solution and saturated sodium chloride solution and then dried over sodium sulfate and concentrated, giving 73.6 g (54%) of a clear oil.

$^1$H NMR (DMSO-d$_6$, 200 MHz): δ: 6.96, m, 4H, aromatic H; 3.43, s, 3H, CH$_3$; 3.11, m, 1H, CH; 2.91, m, 4H, CH$_2$ Step 2: 2-carboxamide-indane (E)

D (102.1 g, 0.58 mol) and 500 ml of concentrated ammonia solution are introduced into an autoclave and the mixture is maintained at 80° C. for 18 hours. The solid thus formed is filtered off with suction and washed with water (63.4 g, 68%).

m.p.=181-183° C.

$^1$H NMR (DMSO-d$_6$, 200 MHz): δ: 7.39, s, 1H, NH; 7.11, m, 4H, aromatic H; 6.85, s, 1H, NH; 3.12-2.97, m, 5H, CH$_2$ and CH Step 3: 2-aminomethyl-indane (F)

A solution of E (63 g, 0.391 mol) in tetrahydrofuran (1.5 l) is added dropwise to a suspension of LiAlH$_4$ (74.15 g, 1.95 mol) in tetrahydrofuran (300 ml) cooled using a cardice/acetone bath, and the mixture is then refluxed for 2 hours. The reaction medium is neutralised (75 ml of water, 75 ml of 5M sodium hydroxide and 225 ml of water) and then filtered. Removal of the solvent leaves an oil (56.9 g, 99%) that quite readily forms a carbonate.

$^1$H NMR (DMSO-$d_6$, 200 MHz): δ: 6.95, m, 4H, aromatic H; 2.90-2.14, m, 7H, 3CH$_2$ and CH; 1.63, s, 2H, NH$_2$ Step 4: 2-(aminoiminomethylamino)methylindane sulfate A mixture of F (20.63 g, 0.140 mol), S-methylisothiourea sulfate (19.5 g, 0.07 mol) and 10 ml of water is maintained at 90° C. for 30 minutes (end of the evolution of methanethiol gas). The crude solid present is recrystallised from a water/ethanol mixture to give 12.7 g (38%) of a white solid.

m.p.=231-233° C.

$^1$H NMR (DMSO-$d_6$, 200 MHz): δ: 7.05, m, 4H, aromatic H; 2.95, m, 2H, CH$_2$; 2.40, m, 5H, 2CH$_2$ and CH $^{13}$C NMR (DMSO-d6, 50 MHz): δ: 157.07, 142.57, quaternary C; 126.59, 124.83, aromatic CH; 45.28, CH$_2$N; 38.74, CH; 36.57, 2CH$_2$

EXAMPLE 4

Synthesis of 2-(aminoiminomethylamino)methylbenzothiophene hydrochloride

Step 1: 2-carboxyethylbenzothiophene (G)

Ethyl 2-mercaptoacetate is added to a solution of dimethylformamide (800 ml), 2-nitrobenzaldehyde (73 g, 0.48 mol) and potassium carbonate (80 g, 0.57 mol) cooled to 0° C., while the temperature is maintained at 0° C. After stirring for 24 hours, the mixture is poured into 2 l of water and this aqueous phase is extracted with ether. The ether phase is dried over sodium sulfate and concentrated. The crude product obtained is purified on a column of alumina (petroleum ether) to give 34 g (35%) of a yellow oil.

$^1$H NMR (DMSO-$d_6$, 200 MHz): δ: 8.04, s, 1H, CH; 7.90, m, 2H, aromatic CH; 7.35, m, 2H, aromatic H; 4.20, q, 2H, CH$_2$; 1.93, t, 3H, CH$_3$ Step 2: 2-carboxamidobenzothiophene (H)

G (34 g, 0.165 mol), concentrated aqueous ammonia (120 ml) and ethanol (50 ml) are maintained at 80° C. in an autoclave for 24 hours. The solution is then concentrated and the crude solid is triturated in isopropyl ether and washed with pentane (26 g, 89%).

m.p.=209-211

$^1$H NMR (DMSO-$d_6$, 200 MHz): δ: 8.59, s, 1H, NH; 8.32, s, 1H, CH; 8.15, m, 2H, aromatic H; 7.89, s, 1H, NH; 7.64, m, 2H, aromatic H Step 3: 2-aminomethylbenzothiophene (I)

A suspension of H (26 g, 0.146 mol) in tetrahydrofuran (500 ml) is added to a suspension of LiAlH$_4$ (33.5 g, 0.88 mol) in tetrahydrofuran (100 ml), and the mixture is refluxed for 6 hours. The reaction medium is then cooled to 0° C. and the excess LiAlH$_4$ is destroyed (33 ml of H$_2$O, 33 ml of 5 molar sodium hydroxide and 99 ml of H$_2$O). After filtration and then concentration, the crude product obtained is purified on a column of silica (dichloromethane and then 4/1 dichloromethane/methanol) to give 13 g (56%) of an oil.

$^1$H NMR (DMSO-d6, 200 MHz): δ: 7.65, m, 2H, aromatic H; 7.12, m, 2H, aromatic H; 7.08, s, 1H, CH; 5.46, m, 2H, NH$_2$; 4.60, d, 2H, CH$_2$ Step 4: 2-(aminoiminomethylamino)ethylbenzothiophene hydrochloride A solution of I (11 g, 0.067 mmol), 1-(aminoiminomethyl)pyrazole hydrochloride (9.8 g, 0.067 mol) and isopropanol (50 ml) is refluxed for 24 hours. The reaction medium is concentrated, and the crude solid is recrystallised from water (7 g, 41%).

m.p.=163-165° C.

$^1$H NMR (200 MHz): δ: 8.44-7.26, m, 9H, aromatic H and exchangeable H; 4.70, d, 2H, CH$_2$ $^{13}$C NMR (DMSO-$d_6$, 50 MHz): δ: 157.56, 141.73, 139.49, 139.36, quaternary C; 124.90, 124.76, 123.88, 122.88, 122.68, aromatic CH; 40.28, CH$_2$ Table 1 summarises the formulae and characteristics of the compounds of the formula (I).

TABLE 1

| Compound | Structure | m.p. in ° C. (Köfler) | $^{13}$C NMR 50 MHz δ ppm |
|---|---|---|---|
| 1 | benzothiazole-CH$_2$-N(CH$_3$)-C(=NH)-NH$_2$ | 203-205 (hydrochloride) | (DMSO-$d_6$) 168.32, 159.08, 154.12, 136.33, quaternary C 128.20, 127.27, 124.30 and 124.15, aromatic CH 53.19, CH$_2$ 38.88, NCH$_3$ |
| 2 | benzimidazole-CH$_2$-NH-C(=NH)-NH$_2$ | 171-173 (hydrochloride) | (DMSO-$d_6$) 158.56, 151.26, 138.98, quaternary C 122.88, 115.76, aromatic CH 40.32, CH$_2$ |

TABLE 1-continued

| Compound | Structure | m.p. in ° C. (Köfler) | $^{13}$C NMR 50 MHz δ ppm |
|---|---|---|---|
| 3 | 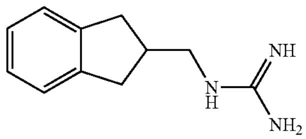 | 231-233 (sulfate) | (DMSO-d$_6$) 157.07, 142.57, quaternary C 126.59, 124.83, aromatic CH 45.28, CH$_2$N 38.74, CH 36.57, 2CH$_2$ |
| 4 | 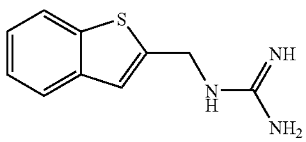 | 163-165 (hydrochloride) | (DMSO-d$_6$) 157.56, 141.73, 139.49, 139.36, quaternary C 124.90, 124.76, 123.88, 122.88, 122.68, aromatic CH 40.28, CH$_2$ |
| 5 | 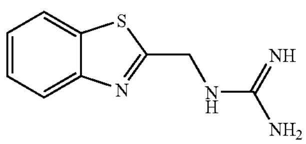 | 196-198 (hydrochloride) | (1H, D2O) 8.20-7.50, m, 4H, aromatic H 5.00, s, 2H, CH$_2$ |
| 6 | 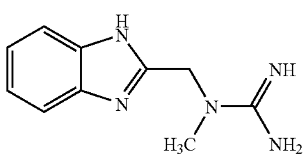 | 253-255 (hydrochloride) | (1H, D2O) 7.80-7.25, m, 4H, aromatic H 4.90, s, 2H, CH$_2$ 3.20, s, 3H, NCH$_3$ |
| 7 | 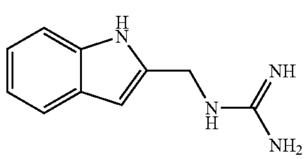 | Decomposes >130 (carbonate) | (DMSO-d$_6$) 160.90, 157.71, 136.73, 135.58, 128.08, quaternary C 121.37, 120.16, 119.30, 111.59, 100.08, aromatic CH 38.51, CH$_2$ |
| 8 | 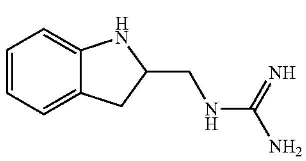 | 189-191 (hemisulfate) | (DMSO-d$_6$) 157.68, 151.74, 127.89, quaternary C 127.40, 124.66, 117.33, 108.75, aromatic CH 57.99, CHN 46.50, CH$_2$N 33.55, CH$_2$ |
| 9 | 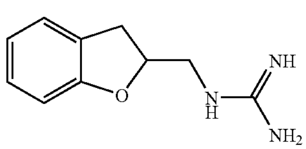 | 139-141 (carbonate) | (DMSO-d$_6$) 159.10, 126.84, quaternary C 128.27, 125.57, 120.84, 109.49, aromatic CH 81.04, CHO 44.87, CH$_2$N 32.56, CH$_2$ |
| 10 | 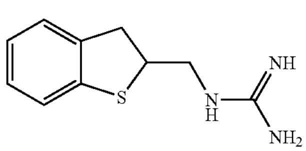 | 187-189 (carbonate) | (DMSO-d$_6$) 160.88, 139.93, 138.91, quaternary C 127.83, 125.53, 124.72, 122.31, aromatic CH 48.46, CHS 45.54, CH$_2$N 38.97, CH$_2$ |

TABLE 1-continued

| Compound | Structure | m.p. in ° C. (Köfler) | $^{13}$C NMR 50 MHz δ ppm |
|---|---|---|---|
| 11 | (5,6-dimethoxy-indan-2-yl-methyl guanidine) | 191-193 (sulfate) | (DMSO-$d_6$) 157.54, 148.11, 134.07, quaternary C 108.80, aromatic CH 55.89, $CH_3O$ 45.77, $CH_2N$ 39.22, CH 36.76, $CH_2$ |
| 12 | (5-methoxy-1-methyl-indol-2-yl-methyl guanidine) | 233-235 (sulfate) | (DMSO-$d_6$) 157.33, 153.86, 136.64, 133.10, 127.45, quaternary C 111.38, 110.51, 102.24, 100.20, aromatic CH 55.66, $CH_3O$ 30.00, $CH_2N$ |
| 13 | (5-methoxy-indol-2-yl-methyl guanidine) | 213-215 (sulfate) | (DMSO-$d_6$) 162.77, 158.79, 141.39, 137.09, 133.67, quaternary C 117.47, 116.40, 107.18, 105.15, aromatic CH 60.81, $OCH_3$ 43.84, $CH_2N$ |
| 14 | (5-fluoro-1-methyl-indol-2-yl-methyl guanidine) | 181-183 (hydrochloride) | (DMSO-$d_6$) 157.80, 148.00, 134.80, 127.00, quaternary C 11.02, 109.50, 104.80, 100.30, aromatic CH 37.72, $CH_2$ 30.28, $CH_3$ |
| 15 | (benzofuran-2-yl-methyl guanidine) | 244-247 (sulfate) | (DMSO-$d_6$) 157.75, 154.49, 128.33, quaternary C 124.46, 123.23, 121.48, 111.35, 104.33, aromatic CH 39.92, $CH_2$ |
| 16 | (N-methyl-N-(indenyl-methyl) guanidine) | 209-211 (hydrochloride) | (DMSO-$d_6$) 157.31, 144.40, 143.51, quaternary C 128.22, 126.66, 124.80, 124.04, 120.96, aromatic CH 50.46, 40.33, $CH_2$ 36.75, CH3 |
| 17 | (5,6-difluoro-indan-2-yl-methyl guanidine) | >250 (sulfate) | (TFA) 158.30, 154.00, 149.00, 139.00, quaternary C 114.5, aromatic CH 47.26, 37.12, $CH_2$ 40.30, CH |

Results of the pharmacological studies will be given hereinbelow.

Study of the Antidiabetic Activity in Nostz Rats

The oral antidiabetic activity of the compounds of the formula (I) was determined on an experimental model of non-insulin-dependent diabetes, induced in the rats with steptozotocin.

The model of non-insulin-dependent diabetes is obtained in the rats by means of a neonatal injection (on the day of birth) of steptozotocin.

The diabetic rats used are eight weeks old. The animals are housed, from the day of birth to the day of the experiment, in an animal house at a regulated temperature of 21 to 22° C. and subjected to a fixed cycle of light (from 7 a.m. to 7 p.m.) and darkness (from 7 p.m. to 7 a.m.). Their food consisted of a maintenance diet, and water and food were given "ad libitum", with the exception of fasting two hours before the tests, during which period the food is removed (post-absorptive state).

The rats are treated orally for one (D1) or four (D4) days with the test product. Two hours after the final administration of the product and 30 minutes after the animals have been anaesthetised with pentobarbital sodium (Nembutal®), a 300 µl blood sample is taken from the end of the tail.

By way of example, results obtained are collated in Table 2. These results show the efficacy of the compounds of the formula (I) in reducing glycaemia in the diabetic animals. These results are expressed as a percentage change in the glycaemia on D1 and D4 (number of days of treatment) relative to D0 (before the treatment).

TABLE 2

| Compound | 20 mg/kg/day | | 200 mg/kg/day | |
|---|---|---|---|---|
|  | D1 | D4 | D1 | D4 |
| 1 | +5 | −4 | −9 | −23 |
| 2 | −17 | −13 | −10 | −25 |
| 3 | +2 | −10 | −14 | −29 |
| 5 | −18 | −3 | −30 | −26 |
| 6 | +3 | 0 | −6 | −16 |
| 7 | −5 | −9 | −19 | −28 |
| 8 | −7 | −12 | −10 | −9 |
| 10 | −3 | −5 | −21 | −25 |
| 11 | −1 | −8 | −8 | −14 |
| 12 |  |  | −22 | −26 |
| 13 |  |  | −16 | −26 |
| 15 | −23 | −28 | −29 | −31 |

The invention claimed is:

1. Compounds of the general formula (I)

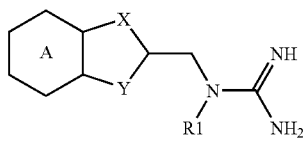

(I)

in which:

A represents a benzene or pyridine ring optionally substituted by one or more of the following groups:
  branched or unbranched $(C_1-C_{20})$alkyl,
  OR2, where R2 represents:
    H,
    branched or unbranched $(C_1-C_5)$alkyl,
    $(C_3-C_8)$cycloalkyl, or
    benzyl,
  NR3R4, where R3 and R4 represent, independently of each other:
    H,
    branched or unbranched $(C_1-C_{20})$alkyl,
    benzyl,
    acetyl,
    $(C_3-C_8)$cycloalkyl,
    or alternatively R3-R4 together form a 3- to 8-membered ring including a nitrogen atom,
  SR5, where R5 represents:
    H,
    branched or unbranched $(C_1-C_5)$alkyl,
    $(C_3-C_8)$cycloalkyl, or
    benzyl,
  halogen
  cyano
  nitro
  $CO_2R6$, where R6 represents:
    H or
    branched or unbranched $(C_1-C_5)$alkyl, or
  trifluoromethyl,
X represents a —CH=, —CH$_2$—, —NH= or —NH— radical,
Y represents a CH$_2$ radical, an oxygen or sulfur atom or a group —NR7, where R7 represents:
  H,
  branched or unbranched $(C_1-C_5)$alkyl,
  benzyl,
  $(C_3-C_8)$cycloalkyl, or
  a $CH_2CO_2H$ group,
R1 represents one of the following groups
  H,
  branched or unbranched $(C_1-C_5)$alkyl, or
  benzyl,
or tautomeric, enantiomeric, diastereoisomeric or epimeric forms or solvates or pharmaceutically acceptable salts thereof,
with the exception of the compounds of the formula (I) in which:
  a—A represents an optionally substituted a benzene ring, X represents —CH= or —CH$_2$—, Y represents an oxygen atom and R1 is a hydrogen atom;
  b—A represents a benzene ring substituted with a halogen atom or an alkyl or alkoxy group having 1-6 carbon atoms, X represents —CH=, Y represents a sulfur atom and R1 is a hydrogen atom,
  c—A represents an unsubstituted benzene ring, X represents —CH$_2$—, R1 is a hydrogen atom or a branched or unbranched $(C_1-C_5)$alkyl radical and Y represents NR7, where R7 represents a hydrogen atom, a branched or unbranched $(C_1-C_5)$alkyl radical or a benzyl radical,
  d—A represents an unsubstituted benzene ring, X represents —CH=, R1 is a hydrogen atom and Y represents NR7, where R7 represents an ethyl radical,
  e—A represents a benzene ring, x represents —CH=, R1 is a hydrogen atom and y represents a sulfur atom.

2. Compounds of the formula (I) according to claim 1, in which the alkyl radicals are $C_1-C_5$ alkyl radicals.

3. Compounds of the formula (I) according to claim 1, in which A represents an optionally substituted benzene ring.

4. Compounds of the formula (I) according to claim 1, in which Y represents a —CH$_2$— radical, a sulfur atom or a group —NR7.

5. Compounds of the formula (I) according to claim 4, in which Y is a sulfur atom and A represents a benzene ring monosubstituted in a position other than position 5' of the double ring, or a benzene ring substituted by at least two groups.

6. Compounds of the formula (I) according to claim 4, in which Y is a group —NR7 and A represents a substituted beuzene ring.

7. Compounds of the formula (I) according to claim 1, in which Y is an oxygen atom, X represents a —CH= radical or a —CH$_2$— radical, and A is a substituted benzene ring.

8. Compounds of the formula (I) according to claim 1, in which Y is an oxygen atom and X represents an —N= or —NH— radical.

9. A process for preparing a compound according to claim 1, comprising the reaction of a compound of the general formula (II)

15

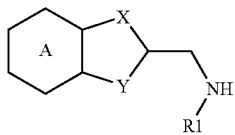
(II)

in which A, X, Y and R1 are as defined in claim 1, with a guanidylating agent.

10. A pharmaceutical composition comprising a compound according to claim 1, and a pharmaceutically acceptable carrier.

11. A method for the treatment of a pathology associated with insulin resistance syndrome, comprising administering a compound of formula (I):

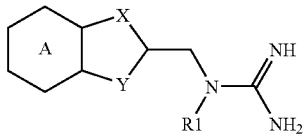
(I)

in which:
A represents a benzene or pyridine ring optionally substituted by one or more of the following groups:
branched or unbranched $(C_1-C_{20})$alkyl,
OR2, where R2 represents:
H,
branched or unbranched $(C_1-C_5)$alkyl,
$(C_3-C_8)$cycloalkyl, or
benzyl,
NR3R4, where R3 and R4 represent, independently of each other:
H,
branched or unbranched $(C_1-C_{20})$alkyl,
benzyl,
acetyl,
$(C_3-C_8)$cycloalkyl,
or alternatively R3 and R4 together form a 3- to 8-membered ring including a nitrogen atom,
SR5, where R5 represents:
H,
branched or unbranched $(C_1-C_5)$alkyl,
$(C_3-C_8)$cycloalkyl, or
benzyl,
halogen
cyano
nitro
$CO_2R6$, where R6 represents:
H or
branched or unbranched $(C_1-C_5)$alkyl, or
trifluoromethyl,
X represents a —CH═, —CH$_2$—, —N═ or —NH— radical,
Y represents a CH$_2$ radical, an oxygen or sulfur atom or a group —NR7, where R7 represents:
H,
branched or unbranched $(C_1-C_5)$alkyl,
benzyl,
$(C_3-C_8)$cycloalkyl, or
a CH$_2$CO$_2$H group,

16

R1 represents one of the following groups
H,
branched or unbranched $(C_1-C_5)$alkyl, or
benzyl
or tautomeric, enantiomeric, diastereoisomeric or epimeric forms thereof, or solvates or pharmaceutically acceptable salts thereof.

12. A method according to claim 11, in which the pathology is diabetes.

13. A method according to claim 11, in which the pathology is dyslipidaemia.

14. A method according to claim 11, in which the pathology is obesity.

15. A method according to claim 14, in which the pathology is atherosclerosis, retinopathies or neuropathies.

16. Compounds of the general formula (I)

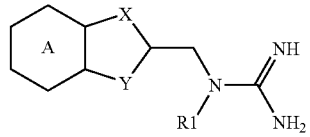
(I)

in which:
A represents a benzene or pyridine ring optionally substituted by one or more of the following groups:
OR2, where R2 represents:
H,
$(C_3-C_8)$cycloalkyl, or
benzyl,
NR3R4, where R3 and R4 represent, independently of each other:
H,
branched or unbranched $(C_1-C_{20})$alkyl,
benzyl,
acetyl,
$(C_3-C_8)$cycloalkyl,
or alternatively R3 and R4 together form a 3- to 8-membered ring including a nitrogen atom,
SR5, where R5 represents:
H,
branched or unbranched $(C_1-C_5)$alkyl,
$(C_3-C_8)$cycloalkyl, or
benzyl,
cyano
nitro
$CO_2R6$, where R6 represents:
H or
branched or unbranched $(C_1-C_5)$alkyl, or
trifluoromethyl,
X represents a —CH═, —CH$_2$—, —N═ or —NH— radical,
Y represents a CH$_2$ radical, an oxygen or sulfur atom or a group —NR7, where R7 represents:
H,
branched or unbranched $(C_1-C_5)$alkyl,
benzyl,
$(C_3-C_8)$cycloalkyl, or
a CH$_2$CO$_2$H group,
R1 represents one of the following groups
H,
branched or unbranched $(C_1-C_5)$alkyl, or
benzyl, or tautomeric, enantiomeric, diastereoisomeric or epimeric forms or solvates or pharmaceutically acceptable salts thereof,
with the exception of the compounds of the formula (I) in which:
a - A represents an optionally substituted benzene ring, X represents —CH= or —CH$_2$—, Y represents an oxygen atom and R1 is a hydrogen atom;
c - A represents an unsubstituted benzene ring, X represents —CH$_2$—, R1 is a hydrogen atom or a branched or unbranched (C$_1$-C$_5$)alkyl radical and Y represents NR7, where R7 represents a hydrogen atom, a branched or unbranched (C$_1$-C$_5$)alkyl radical or a benzyl radical,
d - A represents an unsubstituted benzene ring, X represents —CH=, R1 is a hydrogen atom and Y represents NR7, where R7 represents an ethyl radical,
e - A represents a benzene ring, x represents —CH=, R1 is a hydrogen atom and y represents a sulfur atom.

17. Compounds of the general formula (I)

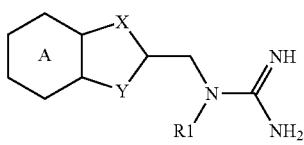

(I)

in which:
A represents a benzene or pyridine ring optionally substituted by one or more of the following groups:
branched or unbranched (C$_1$-C$_{20}$)alkyl,
OR2, where R2 represents:
　H,
　branched or unbranched (C$_1$-C$_{20}$)alkyl,
　(C$_3$-C$_8$)cycloalkyl, or
　benzyl,
NR3R4, where R3 and R4 represent, independently of each other:
　H,
　branched or unbranched (C$_1$-C$_{20}$)alkyl,
　benzyl,
　acetyl,
　(C$_3$-C$_8$)cycloalkyl,
　or alternatively R3 and R4 together form a 3- to 8-membered ring including a nitrogen atom,
SR5, where R5 represents:
　H,
　branched or unbranched (C$_1$-C$_5$)alkyl,
　(C$_3$-C$_8$)cycloalkyl, or
　benzyl,
cyano
nitro
CO$_2$R6, where R6 represents:
　H or
　branched or unbranched (C$_1$-C$_5$)alkyl, or
trifluoromethyl,
X represents a —CH=, —CH$_2$—, —N= or —NH— radical,
Y represents a CH$_2$ radical, an oxygen or sulfur atom or a group —NR7, where R7 represents:
　H,
　branched or unbranched (C$_1$-C$_5$)alkyl,
　benzyl,
　(C$_3$-C$_8$)cycloalkyl, or
　a CH$_2$CO$_2$H group,
R1 represents one of the following groups
　H,
　branched or unbranched (C$_1$-C$_5$)alkyl, or
　benzyl,
or tautomeric, enantiomeric, diastereoisomeric or epimeric forms or solvates or pharmaceutically acceptable salts thereof,
with the exception of the compounds of the formula (I) in which:
a - A represents an optionally substituted benzene ring, X represents —CH= or —CH$_2$—, Y represents an oxygen atom and R1 is a hydrogen atom;
b - A represents a benzene ring, optionally substituted with halogen or an alkyl or alkoxy group having 1-6 carbon atoms, X is —CH=, Y is S and R1 is hydrogen,
c - A represents an unsubstituted benzene ring, X represents —CH$_2$—, R1 is a hydrogen atom or a branched or unbranched (C$_1$-C$_5$)alkyl radical and Y represents NR7, where R7 represents a hydrogen atom, a branched or unbranched (C$_1$-C$_5$)alkyl radical or a benzyl radical,
d - A represents an unsubstituted benzene ring, X represents —CH=, R1 is a hydrogen atom and Y represents NR7, where R7 represents an ethyl radical,
e - A represents a benzene ring, x represents —CH=, R1 is a hydrogen atom and y represents a sulfur atom.

* * * * *

UNITED STATES PATENT AND TRADEMARK OFFICE
CERTIFICATE OF CORRECTION

PATENT NO. : 7,491,733 B2  Page 1 of 1
APPLICATION NO. : 10/472228
DATED : February 17, 2009
INVENTOR(S) : Moinet et al.

It is certified that error appears in the above-identified patent and that said Letters Patent is hereby corrected as shown below:

Column 14, line 8 reads "X represents a –CH=, –CH2–, –NH= or –NH–" should read --X represents a –CH=, –CH2–, –N= or –NH– --

Signed and Sealed this

Twelfth Day of May, 2009

JOHN DOLL
*Acting Director of the United States Patent and Trademark Office*